United States Patent
Fisher et al.

(10) Patent No.: US 7,637,263 B2
(45) Date of Patent: Dec. 29, 2009

(54) METHOD OF CONTROLLING BODY TEMPERATURE WITH AN ELECTROCHEMICAL DEVICE WHILE PROVIDING ON-DEMAND POWER TO AN ELECTRICAL DEVICE

(75) Inventors: Tobin J. Fisher, San Francisco, CA (US); Thomas C. Covington, San Francisco, CA (US); Jonathan L. Glassman, Indianapolis, IN (US); Jesse M. Thomas, San Francisco, CA (US); Daniel Braithwaite, Rowland Heights, CA (US)

(73) Assignee: Ardica Technologies, Inc., San Francisco, CA (US)

( * ) Notice: Subject to any disclaimer, the term of this patent is extended or adjusted under 35 U.S.C. 154(b) by 315 days.

(21) Appl. No.: 11/123,838

(22) Filed: May 6, 2005

(65) Prior Publication Data

US 2005/0256555 A1    Nov. 17, 2005

Related U.S. Application Data

(60) Provisional application No. 60/659,340, filed on May 7, 2004.

(51) Int. Cl.
 *A61B 19/00* (2006.01)
(52) U.S. Cl. ......................................... 128/898; 607/96
(58) Field of Classification Search ................ 128/898; 607/96, 108–112; 606/27–31; 604/113; 219/528, 529
See application file for complete search history.

(56) References Cited

U.S. PATENT DOCUMENTS

| | | | |
|---|---|---|---|
| 3,084,241 A | 4/1963 | Carrona | |
| 3,774,589 A | 11/1973 | Kober | |
| 4,846,176 A * | 7/1989 | Golden | 607/104 |
| 5,973,602 A | 10/1999 | Cole, III et al. | 340/584 |
| 6,045,575 A | 4/2000 | Rosen et al. | 607/88 |
| 6,127,058 A | 10/2000 | Pratt et al. | 429/30 |
| 6,268,595 B1 | 7/2001 | Haenel | 219/528 |
| 6,289,888 B1 | 9/2001 | Welles | 126/263.01 |
| 6,589,681 B1 | 7/2003 | Yamanis | 429/34 |
| 6,620,542 B2 | 9/2003 | Pan | 429/41 |
| 6,660,421 B2 | 12/2003 | Merin Celemin et al. | 429/34 |
| 6,823,678 B1 | 11/2004 | Li | 62/3.5 |
| 6,840,955 B2 * | 1/2005 | Ein | 607/108 |
| 2004/0018415 A1 | 1/2004 | Lai et al. | 429/40 |
| 2004/0211189 A1 | 10/2004 | Arnold | 62/3.5 |

* cited by examiner

*Primary Examiner*—Ahmed M Farah
(74) *Attorney, Agent, or Firm*—Lumen Patent Firm

(57) ABSTRACT

Electrochemical devices are utilized as an on-demand personal temperature control system, as well as an on-demand power supply for electrical devices. The electrochemical devices are planar stiff fuel cells flexibly interconnected in a plane by a flexible interconnecting means. This allows the fuel cells to move with respect to each other out of the plane. This further allows it to be nicely integrated in an article of clothing, to minimize negative impact to a body region or to the article of clothing, and to maximize the heat conduction area to a body region. To further integrate and increase ease of operation a control system and sensors could be included to control: (i) on-demand power and/or heat supply, (ii) temperature levels, and/or (iii) power levels for the electrical device(s).

10 Claims, 9 Drawing Sheets

140

1020   1010   1020

1110   1120   1120

1210
1220   1210   1220

METHOD OF CONTROLLING BODY TEMPERATURE WITH AN ELECTROCHEMICAL DEVICE WHILE PROVIDING ON-DEMAND POWER TO AN ELECTRICAL DEVICE

CROSS-REFERENCE TO RELATED APPLICATIONS

The present application claims priority from Provisional Patent Application with Ser. No. 60/569,340 filed on May 7, 2004, the entire content of which is incorporated herein by reference.

FIELD OF THE INVENTION

The present invention relates generally to electrochemical devices such as fuel cells. More particularly, the invention relates to fuel cell systems for controlling the temperature of a body region using the heat generated by a fuel cell system.

BACKGROUND

Nearly all-modern electronic devices require portable electrical power, and power consumption is often a performance bottleneck. Wireless products, such as personal digital assistants, mobile phones, entertainment devices, and next generation laptops in particular have a great demand for sustained power. For long-term, portable operation, fuel cells are an attractive solution. Fuel cells, like batteries, efficiently convert chemical energy into electricity, but have additional advantages, such as higher energy density and the possibility of instant refueling.

In applications related to personal temperature regulation particularly in colder climates, people have several options, e.g. insulating by adding layers of clothing, using battery powered electric heaters or chemical heaters. Insulating clothing has the advantage of being relatively simple and reliable, but has the primary disadvantage of the necessity for "layering" for variable temperatures or activity levels to maintain comfortable body temperature. This often requires carrying unused layers and the cumbersome process of adding and removing layers as conditions change. Battery powered electric heaters have the advantage of providing controllable, distributed heating, but they are constrained by the limited battery energy density. Chemical heaters have the advantage of low cost, lightweight, and good energy density, but do not provide either controllable or distributable heat or electricity, seriously limiting their efficacy.

Accordingly, it would be considered an advance in the art to develop new systems that allow for easy integration of fuel cells into our day-to-day operations and utilize them as an on-demand power supply for the power-hungry wireless products and at the same time utilize these fuel cells as personal temperature regulators.

SUMMARY OF THE INVENTION

The present invention provides new ways that allow for easy integration of electrochemical devices (i.e. fuel cells) in our day-to-day operations and living. These integrated electrochemical devices can be utilized as: (i) an on-demand personal heat supply or temperature control system, and (ii) an on-demand power supply for electrical devices or wireless products. In particular, the invention could be an article of clothing with an on-demand power and heat supply. In one example the on-demand power and heat supply is integrated at the inside of a jacket at the upper spine region. The preferred design of the on-demand power and heat supply is to have the area of heat generation and flux as large as possible. The conducted or radiated heat generated by the electrochemical device is then controlled to a specific temperature level.

The electrochemical device(s) are stiff planar fuel cell devices that are distributed in a plane if two or more of the planar cells are used. The fuel cell devices are capable of delivering electrical power to one or more of the electrical devices carried by the person wearing the article of clothing as well as capable of conducting heat to a body region. The number of fuel cell devices is dependent on the power requirements for the electrical devices as well as the temperature desires by a user.

The planar stiff fuel cells are flexibly interconnected in the plane by a flexible interconnecting means, which allows the stiff planar fuel cell devices to move with respect to each other out of the plane. This further allows the on-demand power and heat supply to be nicely integrated in an article of clothing by a thin/flat design, i.e. it can be hidden away within or inside an article of clothing. The flexible means and the planar fuel cell devices are preferably distributed and sized with the objective to (i) minimize negative impact to a body region or to the article of clothing and (ii) increase the heat conduction or radiation area.

The electrical and fuel connections between the fuel cells (and possibly other related components) are integrated with the flexible interconnecting means. Various examples are provided for the flexible interconnecting means such as: (i) one or more flexible joints or hinges, (ii) a flexible substrate onto which the stiff planar fuel cell devices are affixed and distributed, (iii) an extension from one of the plates of the two or more stiff planar fuel cell devices and of a thickness to allow for the necessary movement, or (iii) a flexible molding over the two or more stiff planar fuel cell devices.

To further integrate and increase ease of operation a control system is included to control the (i) on-demand power and/or heat supply, (ii) temperature levels, and/or (iii) power levels for the electrical device(s). The control system could be integrated in the article of clothing, or could be a wireless remote control device that can be carried by the user. Sensors could be integrated in the article of clothing or with the on-demand power and/or heat supply with the objective to sense the temperature conducted to the body region and/or the temperature at the body region to ensure safe as well as desired temperature control. In a one embodiment, wires are integrated with the article of clothing (e.g. by passing through the material of a jacket) to the electrical device or to the control system.

BRIEF DESCRIPTION OF THE DRAWINGS

The objectives and advantages of the present invention will be understood by reading the following detailed description in conjunction with the drawings, in which.

DETAILED DESCRIPTION

Although the following detailed description contains many specifics for the purposes of illustration, anyone of ordinary skill in the art will readily appreciate that many variations and alterations to the following exemplary details are within the scope of the invention. Accordingly, the following preferred embodiments of the invention are set forth without any loss of generality to, and without imposing limitations upon, the claimed invention.

Figure 1:
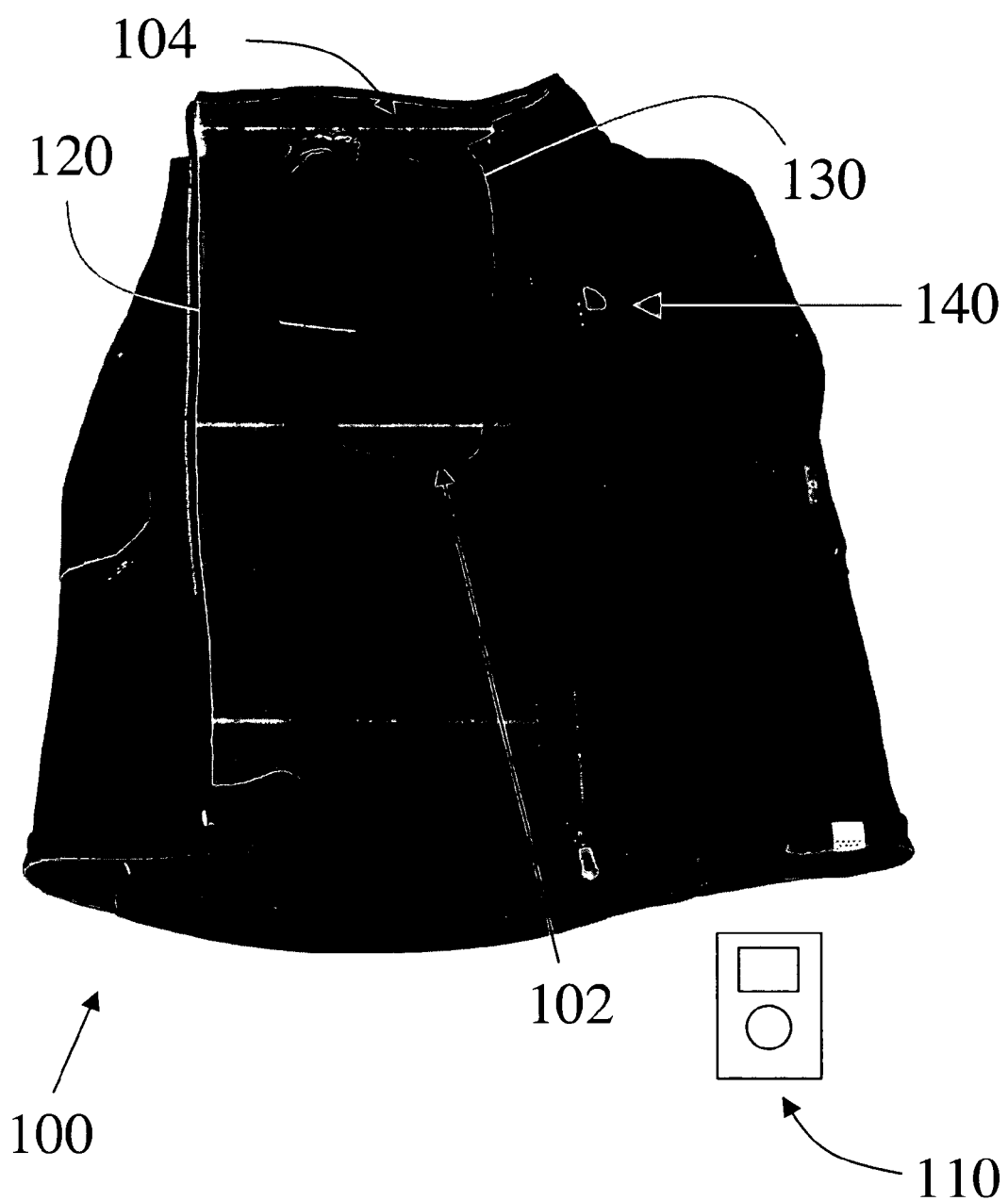
FIG. 1 shows an example of a jacket with an on-demand power supply according to the present invention.

FIG. 1 shows an example of an article of clothing, i.e. a jacket 100, with an on-demand power and heat supply for: (i) providing electrical power to one or more electrical devices 110 and (ii) providing temperature control to a body region. The choice of location for the power and heat supply on a user can significantly affect the effectiveness of the heat transfer into the body. By placing the fuel cell or generator directly over areas of the body which have lower fat deposits, higher blood flow close to the surface of the skin, or dense bone close to the surface of the skin, heat flux to the user can be maximized. Examples of such areas include the front of the rib cage just below the pectoral muscles, the lower back and along the spine (e.g. the upper spine region), the back of the neck, the inside of the wrists and groin, and along the ribcage just below the arm pits.

The idea of the design of the power and heat supply is to maximize the area of the electrochemical devices since this would then maximize the body area to which heat can be conducted. Another objective in the design and integration with an apparel is to develop the on-demand power and heat supply as thin as possible so that it can be easily integrated, e.g. hidden away in the apparel, while meeting the power requirements as desired by the user to power one or more of the electrical devices as well as the desire to heat a particular body region.

Still another key objective for the location of the on-demand power and heat supply is to achieve that it would minimize negative impact to a body region, or to the movement of the body region or the jacket. Examples of such body regions are the upper spine region or the rib cage area, or even parts of the arms in case smaller on-demand power and heat supplies are used.

In the present example of FIG. 1, the on-demand power and heat supply is placed, through an opening at top, inside pocket 102 at the upper spine region. A flap 104 could be used to close the opening of the pocket 102. In general, the power and heat supply of the present invention includes two or more stiff planar fuel cell devices 120 that are distributed in a plane and placed in e.g. a pocket 102 of jacket 100. The number of stiff planar fuel cells in the plane depends on the power requirement. The definition of stiff related to the planar fuel cells is such that minimal deformation occurs during normal use. Stiff planar fuel cells have advantages over fully flexible fuel cells in that they are less likely to be damaged by over bending (bending the fuel cell at a radius small enough to cause damage to the cell) and fatigue (repeated bending at one location). Additionally, the associated manifolding and compression associated with stiff fuel cells tends to enable higher performance (in terms of power per unit area) than fully flexible fuel cells. Semi-flexible fuel cells (fuel cells with flexible interconnects) improve fully flexible fuel cells by enabling more comfortable and functional integration into flexible products.

Figure 2:
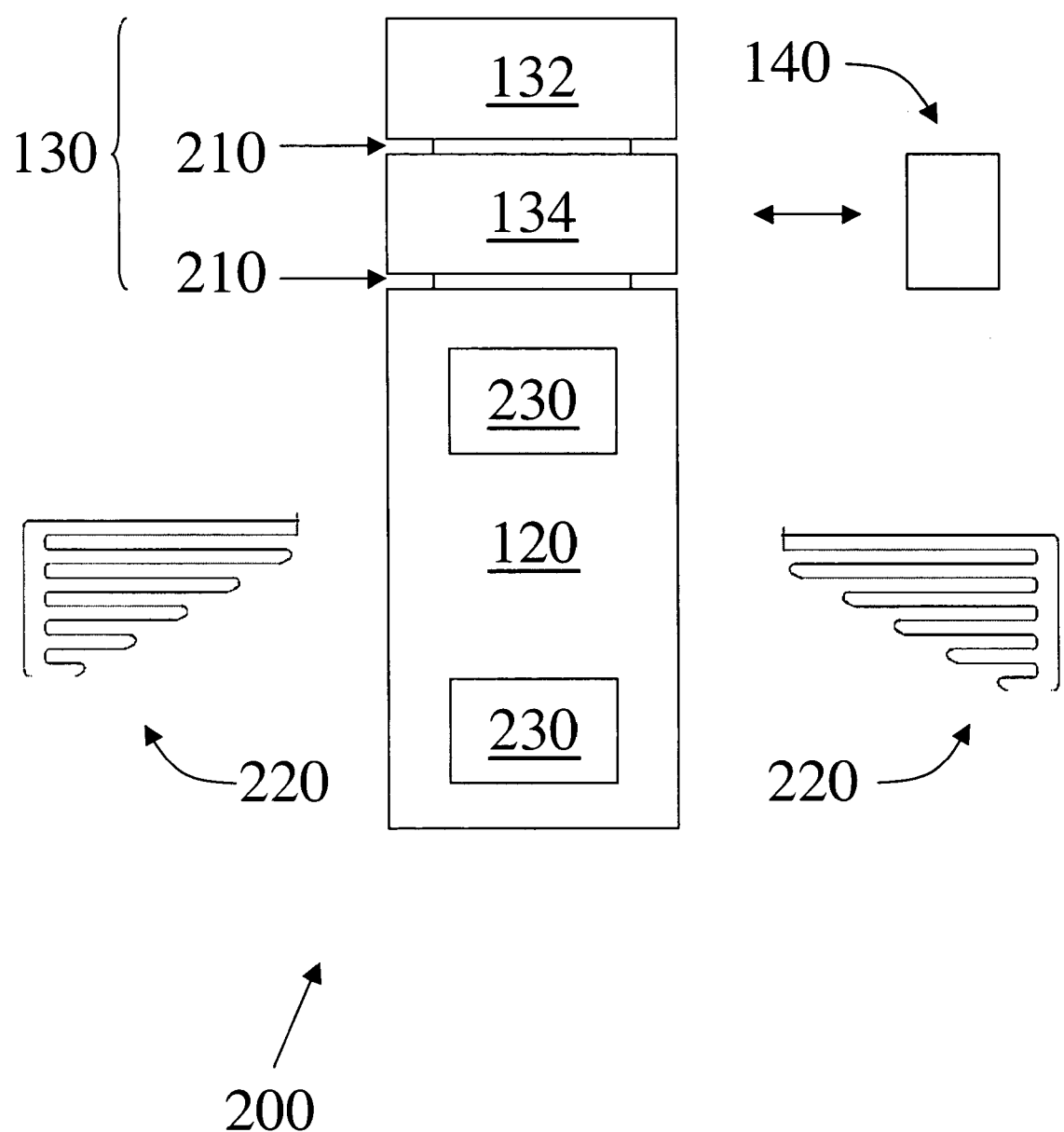
FIG. 2 shows a schematic example of an on-demand power supply according to the present invention.

The present invention is, however, could also have just one fuel cell as long as the power and temperature requirements are met. Other parts 130 of the on-demand power and heat supply are at least a fuel source 134 and a balance of plant 132 that are integrated 210 with the fuel cell devices 120 as further shown by on-demand power supply 200 in FIG. 2. These parts could also contribute to the process of direct heat conduction to the body region that they are covering. Optionally, as shown in FIG. 2 the fuel cells could further power resistive heaters 220, which could be removably attached and used to expand the area of heat flux to the body region. However, it is noted that the primary objective of the present invention is to have the fuel cells be the temperature conductors to the body region its is positioned over. In another aspect of the invention heat conductive elements, materials or layers could be used to further maximize the heat flux (not shown). Examples of these conductive elements are any flexible thermally conductive material (carbon cloth, silver fibers woven into fabric), materials with high in-plane conductivity, but low through plane conductivity as fabric material, or a layer separate to the insulating layer used for the purpose of heat dispersion. Separate layerss could be either on the side of the fabric facing the body or the side of the fabric away from the body.

The fuel cell devices in the present system are electrochemical devices delivering a power density ranging from 0.05 Watt to 1 Watt per $cm^2$. The number of planar fuel cells in the on-demand power and heat supply electrically connected in series will determine the total output voltage. The power density and active area of fuel cell membrane will determine the total power output of the system. Each individual cell will contribute 0.3-0.8 Volts, wherein the total voltage output is determined by the number of cells connected in series. In our system 5 cells, with a total active area of 80 $cm^2$ are used to produce 10 watts electrical and 10 watts heat. These cells operate at a surface temperature range of approximately 80 F to 140 F.

Figure 3:
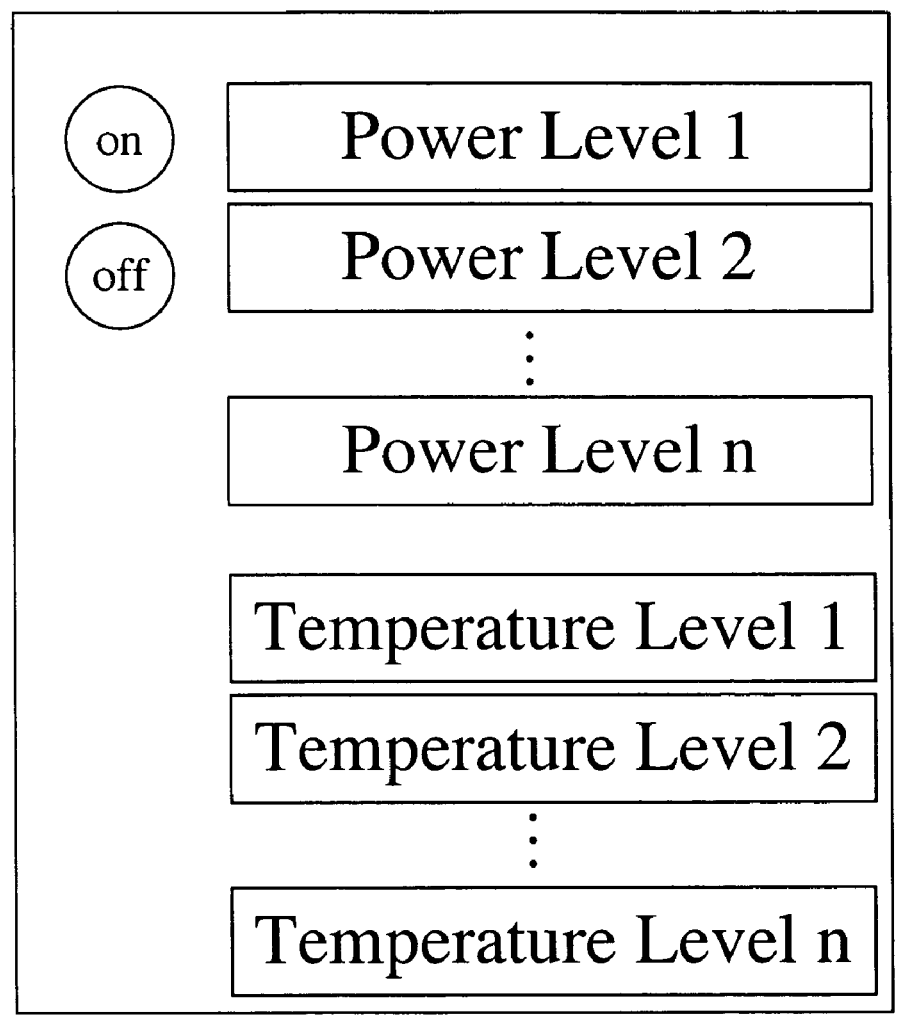
FIG. 3 shows an example of a control system according to the present invention.

A control system 140 to control the power, power level and/or temperature level could either be integrated with the on-demand power and heat supply or positioned in a convenient location to the user. In one example control system 140 is integrated in jacket 100 as illustrated in FIG. 1, either as a remote wireless control system to a user or as a wired control system. The control could be as simple as an on/off mechanism or could have a more sophisticated control loop that sets a particular power level, such as (i) Power level 1, Power level 2 . . . Power level n, or (ii) a more sophisticated control loop that sets a particular temperature level, such as Temperature level 1, Temperature level 2 . . . Temperature level n as shown in FIG. 3. The power output and temperature of the fuel cell is controlled by varying the electrical load on the cells. This can be done by a variety of methods including varying the duty cycle of an intermittent connection between the fuel cell and the load element (Pulse Width Modulation Control) or by varying the resistance of the load element. In the case of warming resistive heaters, the later method could be accomplished by selectively energizing resistive elements of varying resistances. Control system 140 could also include a display to provide feedback on the state or performance of the on-demand power and heat supply.

Sensors 230 could be added and placed on, near or in between the fuel cells and the body region to provide feedback to the balance of plant and/or control system. In some instances, a "closed loop" control mechanism that employs feedback from some number of sensors could be for further control of the active elements. In one possible embodiment, a temperature sensor could be place in contact with the fuel cell to sense the fuel cell surface temperature. In one possible control mechanism, the power output of the fuel cell could be reduced if the fuel cell surface temperature rose above preset limits. In another possible embodiment, the voltage of each fuel cell could be used to provide feedback to the operating condition of the fuel cell. Fuel flow and electrical load on the cell could be varied in response to voltage conditions above or below pre-determined limits. Additionally, pressure sensors could be used to monitor the availability of fuel to the fuel cell.

The electrical power transfer between the on-demand power and heat supply and the electrical device is established via wires that are preferably passing through the article of clothing. Similarly the wires between the control system and the balance of plant are preferably hidden or tucked away in the article in case the control system is not setup as a wireless unit.

To ensure integration of the on-demand power and heat supply in an article of clothing and at the same time maximizing the comfort of wearing and heat transfer to the user, the stiff planar fuel cell devices are distributed and spaced in a plane by flexible interconnecting means. The key objective of the flexible interconnecting means is to allow the stiff planar fuel cell devices to move with respect to each other out of the plane so as to minimize negative impact to (i) a body region by following anatomical features, or (ii) to the movement of the body region or the jacket and to maximize contact with the body, and thus heat transfer. The flexible interconnecting means has either integrated therein or therewith the electrical connections and fuel connections for each of the stiff planar fuel cell devices, which is described herein according to several examples.

Figure 4:
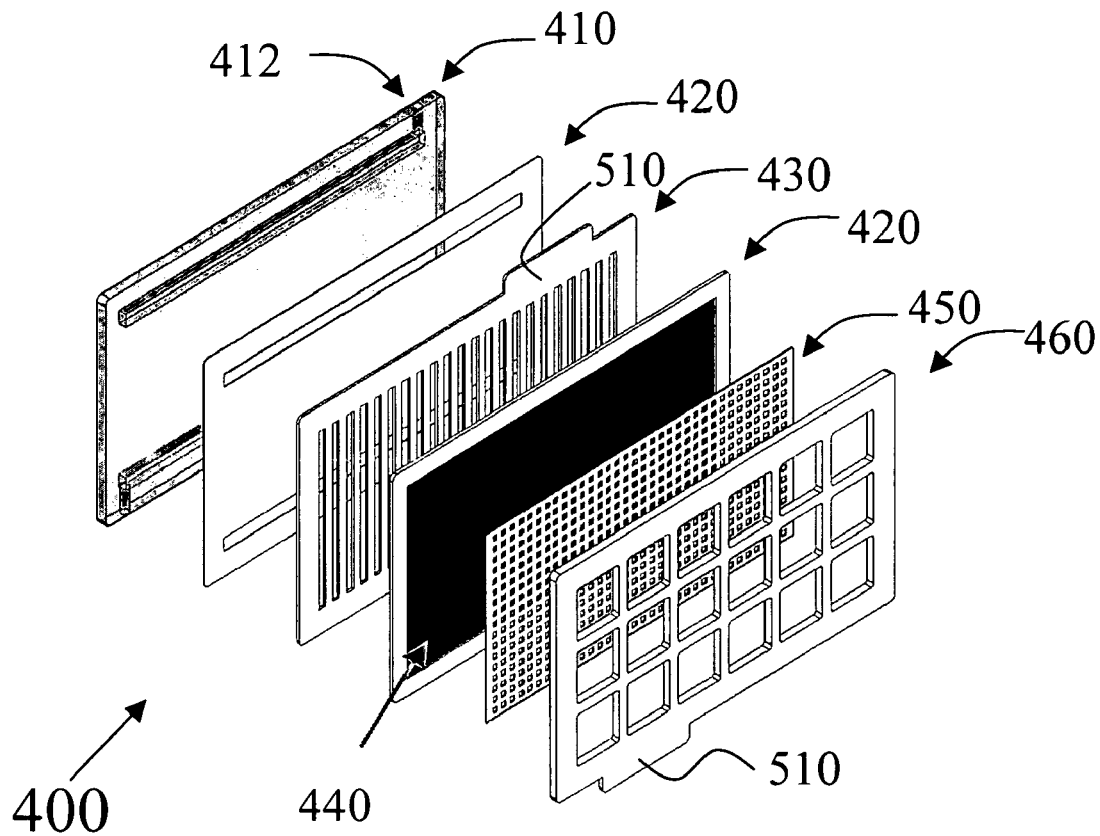
FIGS. 4-5 each show an example of a stiff planar fuel cell according to the present invention.
Figure 5:
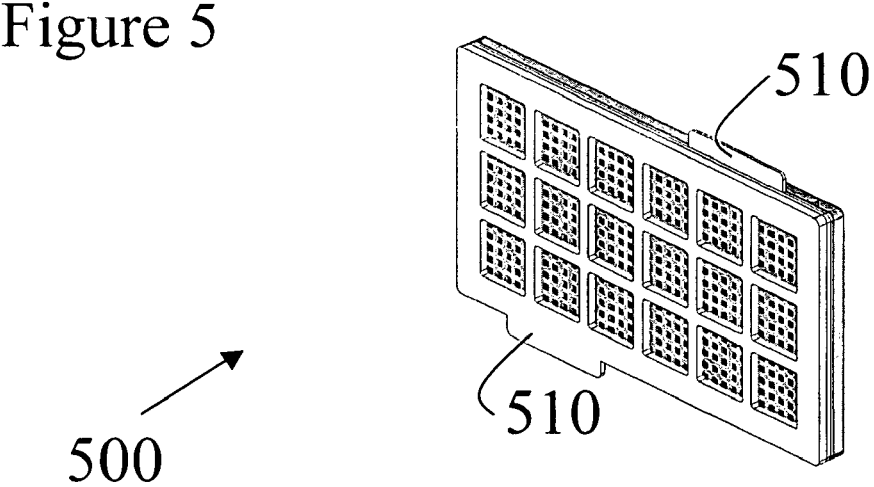

FIG. 4 shows an exploded view 400 of a planar stiff fuel cell with several plates or layers. The planar fuel cell distinguishes a hydrogen gas manifold 410 with a fuel (hydrogen port) 412 and two layers of a bonded adhesive 420, 422 at either side of an anode plate 430. Bonded adhesive layer 422 has disposed thereon a membrane and electrode assembly (MEA) 440 over which a conductive mesh 450 is placed. At the other outside of the planar fuel cell a cathode plate 460 is placed against and over the conductive mesh 450. FIG. 5 shows the assembled stiff planar fuel 500 with two electrical tabs 510 that are used to electrically connect with other fuel cells and eventually with the balance of plant before it connected to an electrical device.

Figure 6:
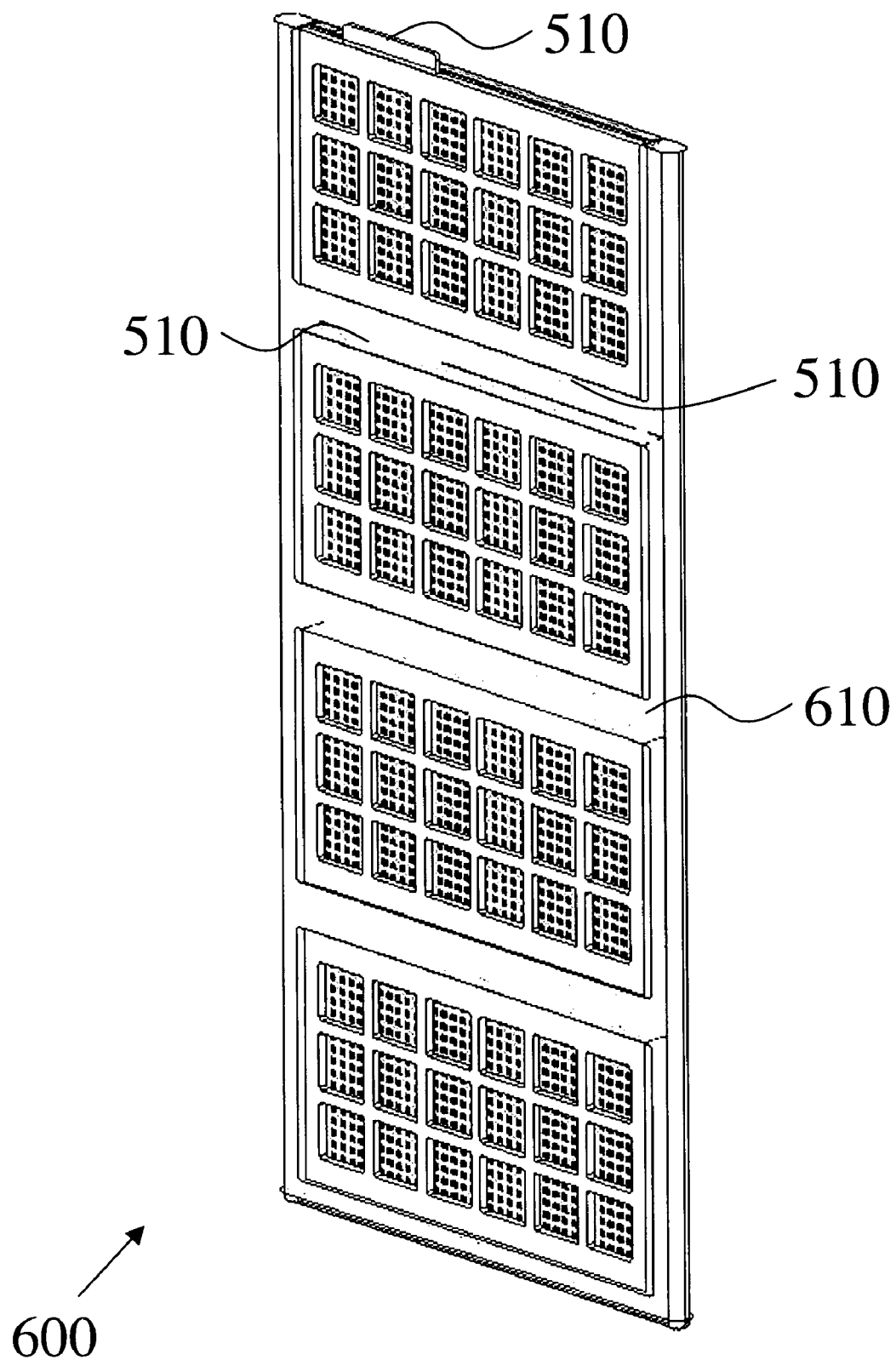
FIG. 6 shows an example of two or more stiff planar fuel cell devices flexibly interconnected according to the present invention.

FIG. 6 shows an example of four stiff planar fuel cells 500 interconnected by flexible means 610, which could be a flexible material that is molded over the fuel cells to create flexible joints in between them. Another objective of the flexible interconnecting means is to include the electrical connection and fuel connections in between the fuel cells, adding strain relief as well as a nicely integrated package with wires or fuel lines hidden as much as possible.

Figure 7:
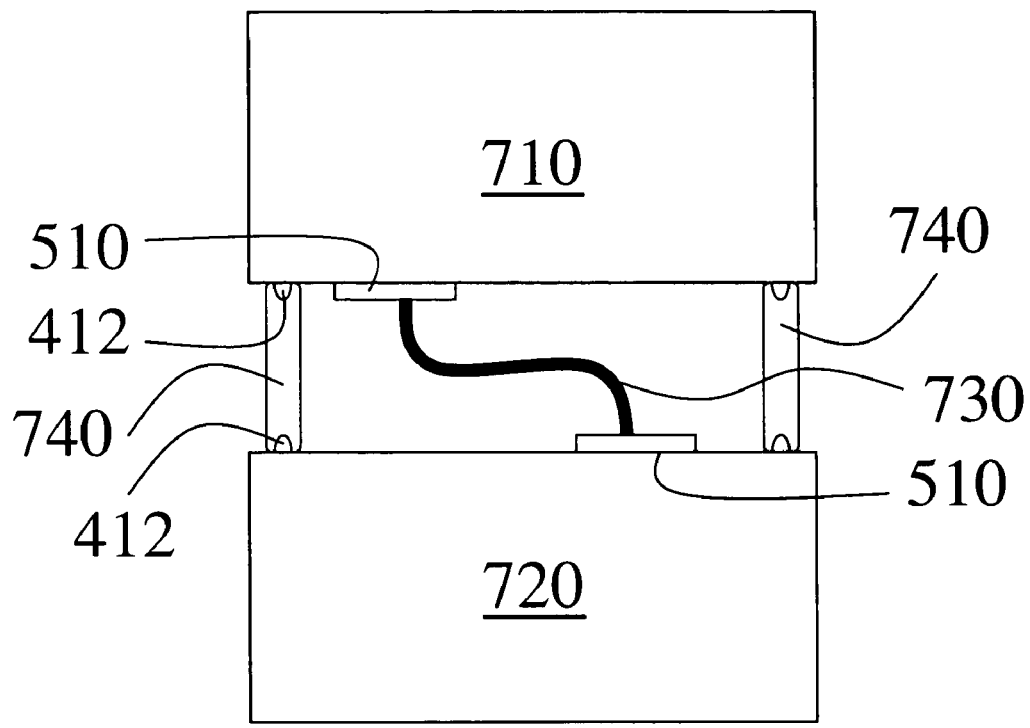
FIGS. 7-8 each show an example of electrical and fuel connections between planar fuel cells according to the present invention.
Figure 8:
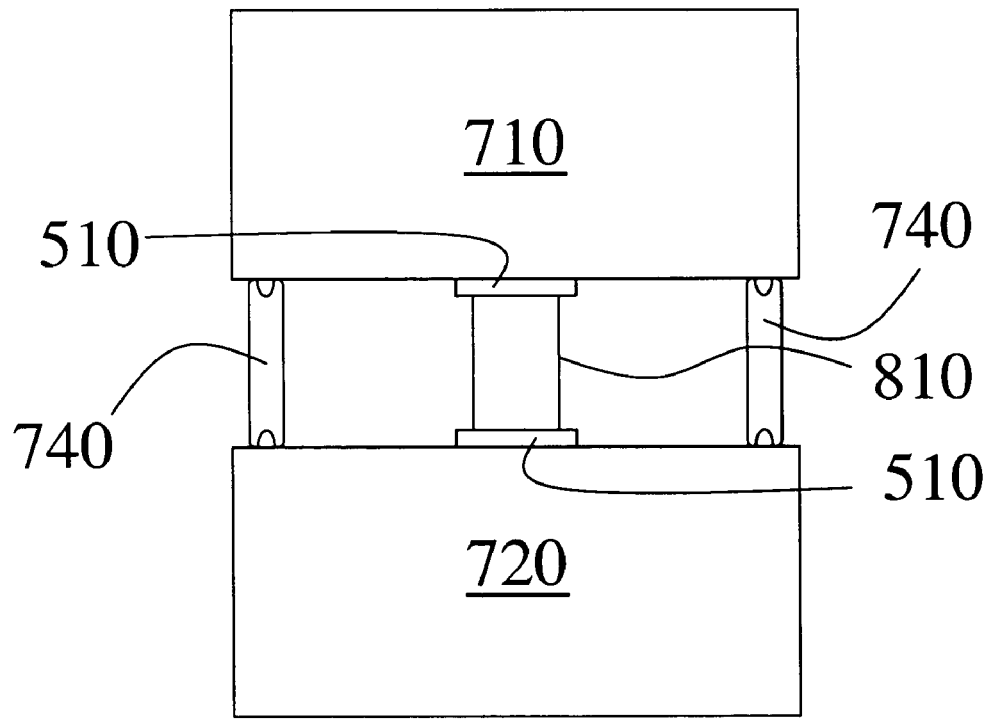

FIGS. 7-8 show some examples of serially connecting the fuel lines and electrical contacts for two planar fuel cells 710, 720. The key objective here is to use materials or designs that maintain the flexibility of the flexible interconnecting means. Therefore, one example could be a flexible wire 730 connecting the two electrical connections 510 of two respective fuel cells. In another example shown in FIG. 8, a flexible metal foil 810 could be used to electrically connect the two electrical connections 510. A person of average skill in the art to which this invention pertains can appreciate that other flexible electrically conducting mechanism or connections can be used. The present invention is therefore not limited to these two exemplary electrical connections.

Figure 9:
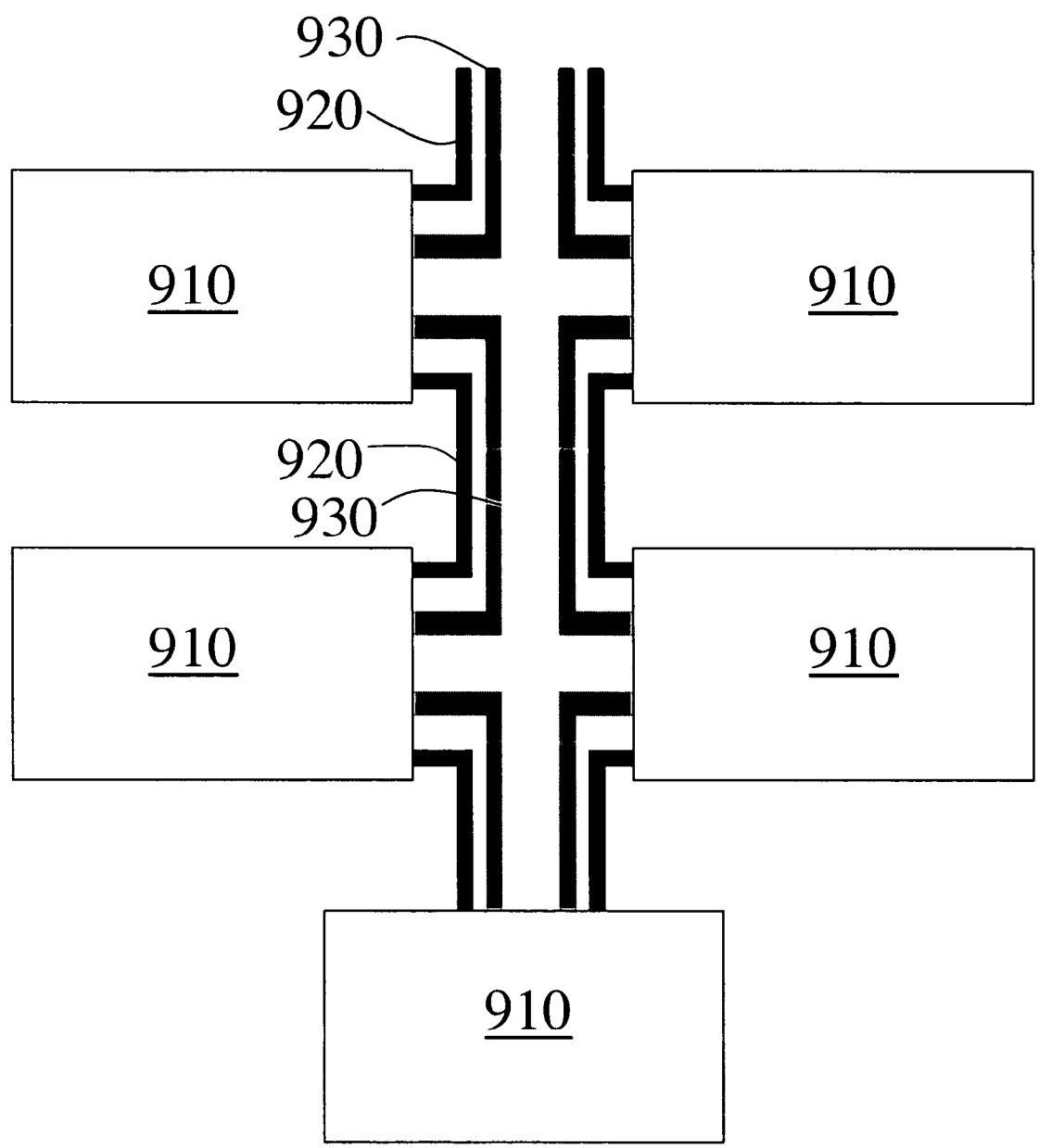
FIG. 9 shows an example of five planar fuel cell devices distributed in a plane according to the present invention.

The fuel connections 740 could also range from a variety of designs and materials such as a flexible fuel line tightly connected to the fuel ports 412. In another example one or more flexible or stiff fuel connectors could be used that are movably connected to the fuel ports 412, e.g. by adding joints or hinges. FIG. 9 shows an example of a configuration of five stiff planar fuel cells 910 and their arrangements for electrical connections 920 and fuel connections 930. A person of average skill in the art to which this invention pertains can appreciate that various different configurations can be designed that are all within the scope of the invention.

Figure 10:
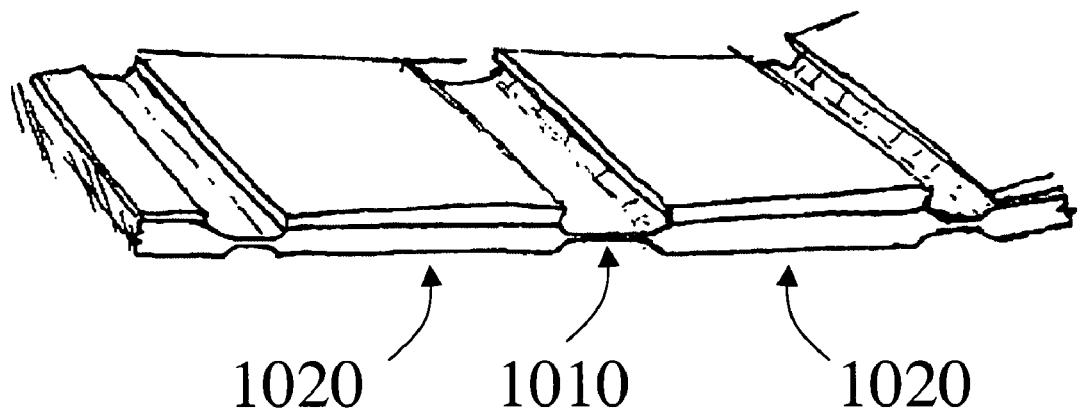
FIGS. 10-13 show examples of flexible interconnecting means according to the present invention.
Figure 11:
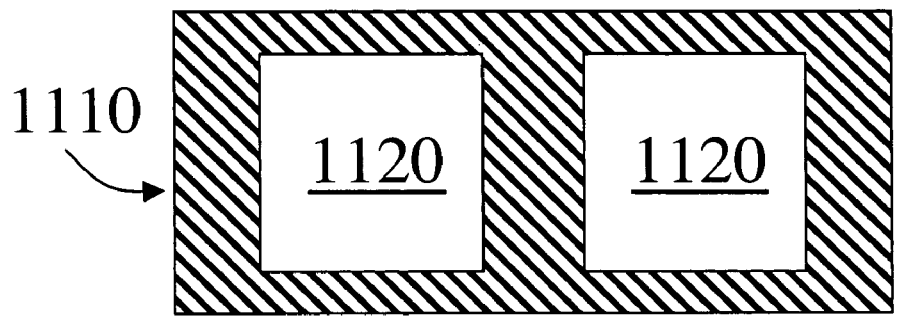
Figure 12:
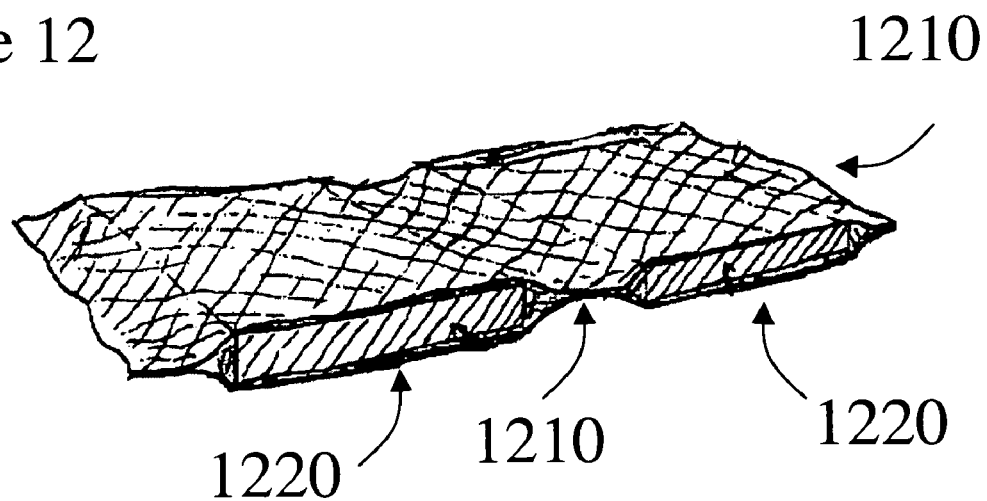
Figure 13:
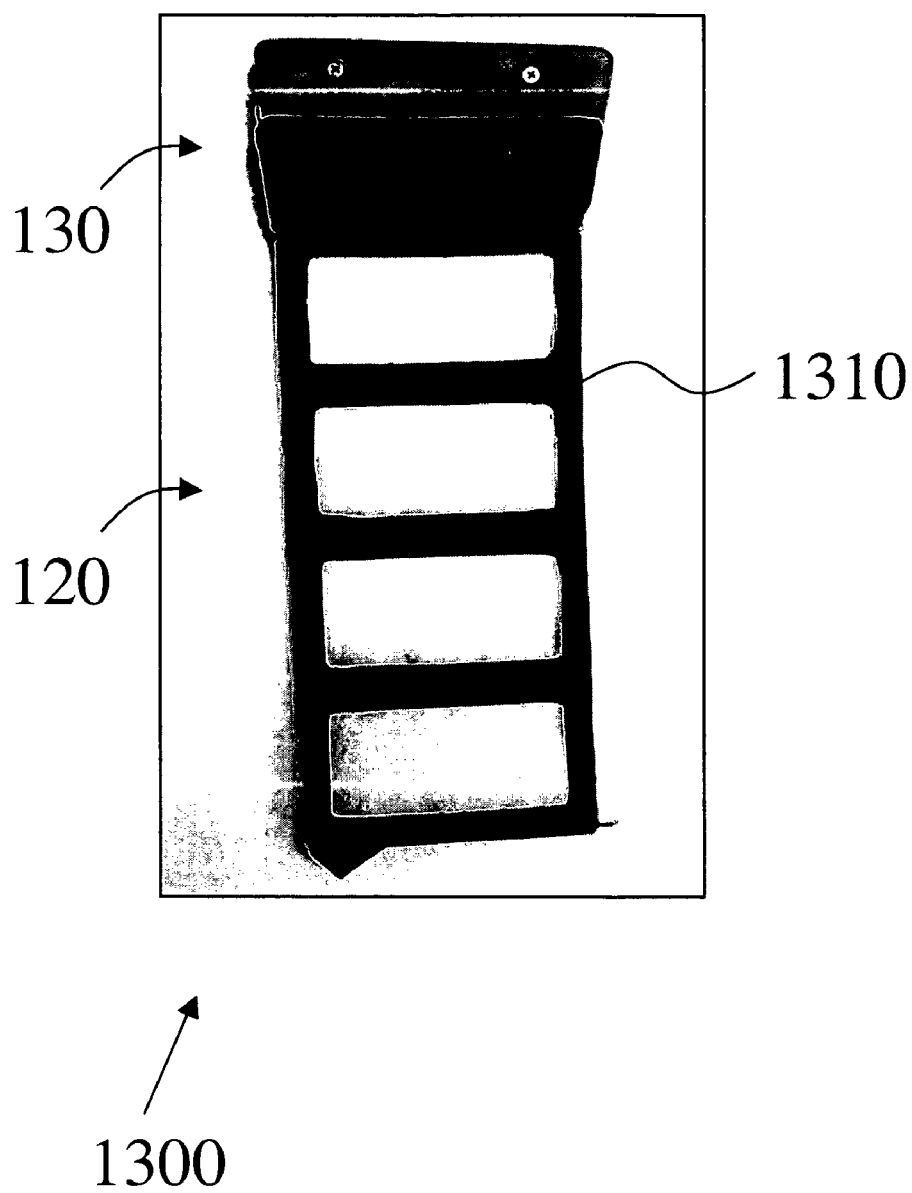

The flexible interconnecting means includes a variety of different ways to ensure (i) a flexible connection between the stiff planar fuel cells, (ii) integration of fuel and electrical connections, and (iii) strain relief for these connections. In one aspect, one or more flexible joints could be used. In another aspect, the fuel and electrical connection could by themselves provide the flexible interconnecting means (FIGS. 7-9). In yet another example joint or hinges 1010 could be added to provide the flexibility between fuel cells 1020 as shown in FIG. 10. In another aspect, a flexible substrate 1110 could be used onto which the two or more stiff planar fuel cell devices 1120 are affixed and distributed as shown in FIG. 11. In yet another aspect, the flexible interconnecting means could be an extension from one of the plates of the fuel cell (e.g. the anode plate) whereby the thickness of the plate is adjusted (e.g. thinned or patterned) so that the flexibility is enabled in between the fuel cells; this could be envisioned by 1010 and 1110 in FIGS. 10-11). As shown in FIG. 6, in still another aspect of the invention the flexible interconnecting means could be established by molding or lamination over the two or more stiff planar fuel cell devices. Such a mold or a laminate could for example be a fabric 1210 as is shown in FIG. 12 where it covers fuel cells 1220. However, in general, the flexible interconnecting means could be established by a variety of methods and flexible materials including, but not limited to, fabrics, flexible polymers (e.g. urethane), rubber, leather, metals, and polymer coated fabrics. FIG. 13 shows an example of the on-demand power and heat supply system of the present invention integrated within flexible interconnecting means 1310.

The fuel cells could be integrated into an article by a number of possible methods. The fuel cells cell may be affixed to an article (e.g. a fabric) by methods including, but not limited to, hook and loop connectors, adhesives, magnets, enclosing them in a pocket sewn into the fabric or removably attachments (e.g. one or more buttons or hooks, Velcro, a zipper, or any other equivalent mechanism or combinations thereof), adhering a fabric layer to the fuel cells and then sewing the perimeter of the fabric layer into the garment, sandwiching the cell between layers of fabric, welding a fabric layer bonded to the cell to the fabric of the garment, or any other magnetic, mechanical, or chemical connectors. In one embodiment, the garment could be offered to a user with the on-demand power supply permanently integrated into the jacket (such that the fuel cartridge may be changed). In another embodiment, the article could be offered to a user with features such that the system could be easily integrated in other applications or apparel. Such features may include, but are not limited to, special pockets for the fuel cell and generators, Velcro attachment points, and embedded wires and/or interface controls.

The on-demand power supply could be used in a wide variety of articles of clothing and applications including, but not limited to, apparel integrated personal climate control (both heating and cooling), apparel integrated health monitoring devices, sports equipment (e.g., skis, snowboards), medical devices, wearable computing devices, augmented reality devices, apparel embedded safety devices such as lights, foldable/rollable power sources (e.g. power supplies for life rafts, tents), apparel integrated communication devices, and portable electronics battery chargers or any other portable power and/or heat sources.

There are a large number of possible applications for the on-demand power and heat supply described above. Three classes of applications include, but are not limited to, using the fuel cell system solely as a source of electrical power, using it for the purpose of combined heat and electrical power, and solely for the purpose of a controllable heat source. Possible applications include, but are not limited to, using the fuel cell system in an article of clothing, sporting equipment, survival equipment, bedding, medical devices, luggage, backpacks, seating, or material transport.

When integrated into an article of clothing, this system could be used for applications including, but not limited to, personal climate control, heated apparel, health monitoring, communications, lighting, powered exoskeleton systems, and powering or recharging electronic devices. Specific embodiments for heated apparel include, but are not limited to, heated jackets, vests, shirts, pants, gloves, mittens, hats, socks, boots, shoes, and goggles. One embodiment for the application of heated shoes and boots is to use a fuel cell and or generator as part of the sole of the shoe or boot.

Examples of sporting equipment applications include, but are not limited to, heated skis and snowboards, and heated ski and snowboard bindings. Examples of survival equipment include, but are not limited to, electrical power and heat for life rafts, heated bivouac bags, and climate controlled tents. Bedding products that could benefit from the fuel cell system described include, but are not limited to, heated sleeping bags, heated sleeping pads, heated blankets, and heated pillows.

Examples of possible medical device products include supplying heat and electric power to patient temperature control devices, and supplying electric power to wearable health monitoring devices. Two possible specific examples of patient temperature control and monitoring devices include a transport device for babies and a transport device for trauma victims. Incorporated into backpacks or other luggage, the fuel cell system could be used for climate control of the wearer or the contents of the luggage or for supplying electrical power to a number of possible electronic devices. An example of a seating application for this technology includes, but is not limited to, heated stadium seat pads or other heated seating devices.

The fuel cell may be integrated into a wide variety of clothing including, but not limited to, outer jackets, inner layers, vests, gloves, hats, pants, socks, shoes, and boots.

Some types of fuel cells are differentiated by their electrolytes—Solid Oxide Fuel Cells, Molten Carbonate Fuel Cells, Alkaline Fuel Cell, Polymer Electrolyte Membrane Fuel Cell, and Phosphoric Acid Fuel Cells. In some embodiments, hydrogen fueled Polymer Electrolyte Membrane (PEM) or PEM fuel cells are used in the application of integrating a fuel cell into flexible form factors. There are a number of alternatives in the design of a PEM fuel cell including the gas distribution material and layout, gas flow structure design, and sealing method, to name just a few. However, it is noted that the present invention uses stiff planar fuel cells rather than a continuous flexible planar fuel cell to maintain high performance and efficiency of the on-demand power supply.

While many alternatives could be used, a substantially flat fuel cell has a number of advantages for integration into products with flexible form factors. With the broad face oriented towards the body, such a cell could be worn with minimal extra bulk or discomfort to the user. When used for the application of heated clothing, such a design would maximize the transfer of heat from the fuel cell to the user. As described above, such a cell could be held together by adhesive bonding around the edges, functioning to seal the gas inside the cell and maintain contact pressure between the electrodes and the charge collectors on the gas distribution plates. A further advantage of using a flat fuel cell for this application is that the system could be either shaped to fit the area of the body that it rests against, or it could be made flexible, so that it conformed to the body of the user as described above.

Oxygen can be supplied to the cathode of the fuel cell by a number of different methods. Alternatives include, but are not limited to, pure oxygen from a contained oxygen source, compressed air from an air compressor, forced flow using a fan, and "free air" breathing using convection and natural air flow to supply fresh air. The choice of oxygen supply affects the power output of the cell and the number of additional components necessary to make the cell functional. Free air breathing cells tend to have the lowest power output per unit area of the cell (currently 150 mW/cm$^2$), but have the advantage of requiring the fewest additional components for operation. For power outputs of approximately 50 Watts and below, free air breathing cells are used in some embodiments for this application. However, in instances where the cathode cannot be exposed to the atmosphere (eg. Divers), higher power outputs are required, or a source of moving air may easily be incorporated into the design (such as when used for cooling via a compressor), or other alternatives may become the preferred embodiment.

Although the present invention and its advantages have been described in detail, it should be understood that the present invention is not limited to or defined by what is shown or discussed herein. The drawings, description and discussion herein show examples of the invention and provide examples of using the invention. One skilled in the art will realize that implementations of the present invention could be made without departing from the principles, spirit or legal scope of the present invention. Accordingly, the scope of the present invention should be determined by the following claims and their legal equivalents.

What is claimed is:

1. A method of providing heat to a body region of a living organism and providing electrical power to an electrical device, comprising:
   (a) interconnecting two or more stiff planar fuel cells or fuel cell devices via a flexible interconnection, wherein said flexible interconnection allows said two or more interconnected stiff planar fuel cells or fuel cell devices to move with respect to each other, wherein said two or more interconnected stiff planar fuel cells or fuel cell devices generate heat while creating useful power;
   (b) placing said two or more interconnected stiff planar fuel cells or fuel cell devices over or near said body region of said living organism, where said stiff planar form optimally commutes heat to said body region, wherein each of said two or more interconnected stiff planar fuel cells or fuel cell devices is capable of positioning against or conforming to the contour of said body region of the moving capability of said flexible interconnection;

(c) transferring heat generated by said two or more interconnected stiff planar fuel cells or fuel cell devices to said body region and its subcutaneous layers of said living organism;

(d) providing at least one electrical device requiring electrical power, wherein said at least one electrical device is connected to said two or more interconnected stiff planar fuel cells or fuel cell devices and carried by said living organism; and (e) powering said at least one electrical device using the generated electrical power by said two or more interconnected stiff planar fuel cells or fuel cell devices.

2. The method as set forth in claim 1, further comprises sensing the temperature near or on said living organism and further controlling said transferring heat to said body region.

3. The method as set forth in claim 1, further comprising controlling said temperature through a control system.

4. The method as set forth in claim 3, wherein said control system is integrated in an article of clothing.

5. The method as set forth in claim 1, further comprising controlling the power to said electrical device through a control system.

6. The method as set forth in claim 5, wherein said control system is integrated in an article of clothing.

7. The method as set forth in claim 1, wherein said stiff planar fuel cells or fuel cell devices is integrated in an article of clothing.

8. The method as set forth in claim 1, wherein said stiff planar fuel cells or fuel cell devices is integrated in an article of clothing in such a way that said stiff planar fuel cells or fuel cell devices is positioned to cover over or near the upper spine region of a mammal.

9. The method as set forth in claim 1, wherein said flexible interconnection has integrated therein or therewith electrical connections and fuel connections for each of said fuel cells or fuel cell devices.

10. The method as set forth in claim 1, wherein said stiff planar fuel cells or fuel cell devices further comprises a heat conducting means.

\* \* \* \* \*